(12) United States Patent
Schnarwiler et al.

(10) Patent No.: US 10,118,764 B2
(45) Date of Patent: Nov. 6, 2018

(54) TRANSPORTING DEVICE FOR TRANSPORTING A LABORATORY DIAGNOSTIC VESSEL CARRIER

(71) Applicant: Roche Diagnostics Operations, Inc., Indianapolis, IN (US)

(72) Inventors: Rolf Schnarwiler, Hochdorf (CH); Beat Jaeggi, Lucerne (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/437,942

(22) Filed: Feb. 21, 2017

(65) Prior Publication Data

US 2017/0253431 A1 Sep. 7, 2017

(30) Foreign Application Priority Data

Mar. 1, 2016 (EP) .................................... 16158114

(51) Int. Cl.
 *B65G 11/08* (2006.01)
 *G01N 35/04* (2006.01)
(52) U.S. Cl.
 CPC .......... *B65G 11/086* (2013.01); *G01N 35/04* (2013.01); *G01N 2035/0406* (2013.01); *G01N 2035/046* (2013.01); *G01N 2035/0467* (2013.01)
(58) Field of Classification Search
 CPC .... B65G 11/081; B65G 11/085; B65G 11/086
 (Continued)

(56) References Cited

U.S. PATENT DOCUMENTS 571,389 A * 11/1896 Pancoast
1,383,318 A * 7/1921 McCormick ............. B65G 1/08
14/69.5
(Continued)

FOREIGN PATENT DOCUMENTS

CH  708128 A1  12/2014
EP  2902790 A1  8/2015
(Continued)

OTHER PUBLICATIONS

Search Report dated Sep. 1, 2016, in Application No. EP 16158114. 5, 9 pages.

*Primary Examiner* — Douglas A Hess
(74) *Attorney, Agent, or Firm* — Roche Diagnostics Operations, Inc.

(57) ABSTRACT

A transporting device for transporting a laboratory diagnostic vessel carrier from a first line portion to a second line portion of a conveying line is disclosed. The first line portion is above the second line portion with respect to gravity. The transporting device comprises first and second transporting portions. The first transporting portion is connected to the first line portion and the second transporting portion is connected to the second line portion. The first transporting portion extends in a first direction and the second transporting portion extends in a second direction different from the first direction. The first and second transporting portions transport the laboratory diagnostic vessel carrier by gravity. The first direction comprises at least a first component and the second direction comprises at least a second component. The second component is opposite to the first component. Further, a conveying line comprising such a transporting device is disclosed.

17 Claims, 3 Drawing Sheets

(58) Field of Classification Search
USPC .......... 198/546, 565; 193/27, 35 SS, 35 MD
See application file for complete search history.

(56) References Cited

U.S. PATENT DOCUMENTS

| | | | | |
|---|---|---|---|---|
| 3,460,660 | A * | 8/1969 | Barrowclough | A47B 81/007 193/27 |
| 3,696,735 | A * | 10/1972 | Boertje | A47J 37/1214 193/27 |
| 5,651,941 | A | 7/1997 | Stark et al. | |
| 5,735,661 | A * | 4/1998 | De Frondeville | B65G 1/08 193/36 |
| 5,941,366 | A | 8/1999 | Quinlan et al. | |
| 6,186,725 | B1 * | 2/2001 | Konstant | B65G 1/08 193/36 |
| 6,206,626 | B1 | 3/2001 | Boochakorn et al. | |
| 6,259,967 | B1 | 7/2001 | Hartlepp et al. | |
| 6,491,154 | B2 * | 12/2002 | Ydoate | B65G 47/31 198/444 |
| 7,553,118 | B1 * | 6/2009 | Doepker | B65G 1/08 198/347.2 |
| 8,232,103 | B2 * | 7/2012 | Miller | G01N 35/04 198/369.5 |
| 9,696,330 | B2 * | 7/2017 | Nemoto | G01N 35/04 |
| 9,851,369 | B2 * | 12/2017 | Reisch | G01N 35/025 |
| 2012/0177547 | A1 | 7/2012 | Fukugaki et al. | |
| 2015/0177268 | A1 | 6/2015 | Reisch et al. | |
| 2015/0233955 | A1 | 8/2015 | Nemoto et al. | |
| 2015/0233957 | A1 | 8/2015 | Riether | |

FOREIGN PATENT DOCUMENTS

| | | |
|---|---|---|
| FR | 1261562 A | 5/1961 |
| WO | 2011/138448 A1 | 11/2011 |
| WO | 2016/012517 A1 | 1/2016 |

\* cited by examiner

TRANSPORTING DEVICE FOR TRANSPORTING A LABORATORY DIAGNOSTIC VESSEL CARRIER

CROSS-REFERENCE TO RELATED APPLICATIONS

This application claims priority to EP 16158114.5, filed Mar. 1, 2016, which is hereby incorporated by reference.

BACKGROUND

The present disclosure relates to a transporting device for transporting a laboratory diagnostic vessel carrier.

Laborsaving for examination work in the medical field has recently proceeded by introducing diverse automated devices. For example, for testing in a hospital, the samples of inpatients and outpatients are collected from several sections of the hospital and collectively processed in an examination room. Test items for each sample are sent from doctors to the examination room by use of an online information processing system. Test results are then reported online from the examination room to the doctors. For many of test items on blood or urine, pretreatment for testing needs to be performed such as centrifugal process, unplugging, dispensing, and the like. It takes much time for engagement in such pretreatment work in total testing working hours.

Next, the flow of a process to be performed by a general automated sample testing system is described. A vessel such as test tube that holds a body fluid such as blood collected from a patient is held by a vessel carrier. Such vessel carriers are known. The vessel carrier holding the vessel such as the test tube is loaded into the general automated sample testing system. Barcode information of the loaded sample is read in the system so that the sample type is recognized. As described above, the centrifugal process, unplugging, dispensing, and the like are performed as the pretreatment for the test process.

The contents of the pretreatment vary depending on the sample type, for example, for a urine test, the centrifugal process does not need to be performed. A sample type that needs to be subjected to the centrifugal separation is a sample on which the unplugging and dispensing are performed after centrifugal separation. The dispensing process usually known as aliquoting is a process in which a child sample is generated from a parent sample. For example, dispensed child samples can be simultaneously transported to multiple analyzers that are connected to the system online. A sample that is completed with all processes is stored in a storage module.

The automated sample testing system is introduced in a relatively large facility where hundreds to thousands samples are processed in a day or even per hour. In such large facility, many samples are collected from one patient for multiple testing such as a biochemical test, an immunological test, a solidification test, and a hematological test. Therefore, the number of sample carriers for the hundreds to thousands patients are needed for loading into the automated sample testing system, and accordingly, a space for installing such a sample testing system is required.

For conveying the respective samples to the multiple analyzers, usually a conveying line is installed. Such a conveying line usually comprises several types of conveying such as conveying belt which are present in different line portions. Also a transport system for vessel carriers can be used as conveying lines. As the space for installing the sample testing system usually should be used in an efficient manner, the conveying line comprises line portions which are arranged one above the other. Thus, there is a need to transport a vessel carrier from one level to another level of the conveying line. A known automated sample testing system transports vessel carriers from a higher level to a lower level by inclined line portions which comprise conveyor belts.

Despite the advantages provided by the latter automated sample testing system, there are still some drawbacks. The installation of inclined line portions comprising conveyor belts involves significant costs for installation and maintenance as these line portions are based on wearing constructional members.

Therefore, there is a need for a transporting device for transporting a laboratory diagnostic vessel carrier from a first line portion to a second line portion of a conveying line, and a conveying line allowing a transport of a vessel carrier from a higher level to a lower level of a conveying line in a simple, cost-effective, and maintenance free manner.

SUMMARY

According to the present disclosure, a transporting device for transporting a laboratory diagnostic vessel carrier from a first line portion to a second line portion of a conveying line is presented. The first line portion is arranged above the second line portion with respect to a direction of gravity. The transporting device can comprise a first transporting portion and a second transporting portion. The first transporting portion can be configured to be connected to the first line portion and the second transporting portion can be configured to be connected to the second line portion. The first transporting portion can extend in a first direction and the second transporting portion can extend in a second direction different from the first direction. The first transporting portion and the second transporting portion can be configured to transport the laboratory diagnostic vessel carrier by gravity. The direction can comprise at least a first component and the second direction can comprise at least a second component. The second component can be opposite to the first component.

In accordance with one embodiment of the present disclosure, a conveying line is also presented. The conveying line can comprise at least a first line portion, a second line portion, and a transporting device. The first line portion can be arranged above the second line portion with respect to a direction of gravity. The first transporting portion can be connected to the first line portion and the second transporting portion can be connected to the second line portion.

Accordingly, it is a feature of the embodiments of the present disclosure to provide a transporting device for transporting a laboratory diagnostic vessel carrier from a first line portion to a second line portion of a conveying line, and a conveying line allowing a transport of a vessel carrier from a higher level to a lower level of a conveying line in a simple, cost-effective, and maintenance free manner. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof can be used in a non-exclusive way. Thus, these terms may both refer to a situation in which, besides the feature introduced by these terms, no further features may be present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it can be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" may not be repeated, non-withstanding the fact that the respective feature or element may be present once or more than once.

Further, as used in the following, the terms "particularly", "more particularly", "specifically", "more specifically" or similar terms may be used in conjunction with optional features, without restricting alternative possibilities. Thus, features introduced by these terms can be optional features and may not be intended to restrict the scope of the claims in any way. The invention may, as the skilled person can recognize, be performed by using alternative features. Similarly, features introduced by "in an embodiment" or similar expressions may be intended to be optional features, without any restriction regarding alternative embodiments, without any restrictions regarding the scope and without any restriction regarding the possibility of combining the features introduced in such way with other optional or non-optional features.

The disclosed transporting device can be configured to transport a laboratory diagnostic vessel carrier from a first line portion to a second line portion of a conveying line. The first line portion can be arranged above the second line portion with respect to a direction of gravity.

According to the disclosed transporting device, the transporting device can comprise a first transporting portion and a second transporting portion. The first transporting portion can be configured to be connected to the first line portion and the second transporting portion can be configured to be connected to the second line portion. The first transporting portion can extend in a first direction and the second transporting portion can extend in a second direction different from the first direction. The first transporting portion and the second transporting portion can be configured to transport the laboratory diagnostic vessel carrier by gravity. The first direction can comprise at least a first component and the second direction can comprise at least a second component. The second component can be opposite to the first component.

The term "laboratory diagnostic vessel" as used herein can refer to any type of container suitable to store a sample or reagent in the field of analytics such as, for example, medical analytics. Such vessels can usually be designed as tubes. The term "laboratory diagnostic vessel carrier" as used herein can basically refer to any device configured to hold one or more laboratory diagnostic vessels and to be supplied through a conveying line. Thus, the vessel carrier may be configured as a single vessel carrier suitable to receive a single laboratory diagnostic vessel or a rack suitable to receive a plurality of vessels. Without any restriction, embodiments are described with reference to test tube holders. Such a test tube holder can hold one single test tube containing a sample or reagent and convey the test tube via a conveyor line to different modules of an automated sample testing system. The test tube holder can comprise a housing with a spring for fixing a test tube, a test tube holder body housing, and a bottom lid housing. The housing with a spring for fixing a test tube can have a columnar structure whose center part can be roundly bored so as to allow the insertion of the test tube and can be provided with spring parts inside projecting parts extending upward. It can be noted that the housing with a spring can usually have a columnar shape, but it may have any shape as long as the housing can vertically hold the test tube by the spring parts provided equidistantly or equiangularly, and an outer shape of the housing may be a polygonal column shape. The test tube holder body housing can have a cylindrical shape and can have a cavity part therein. In the cavity part, a tag with a unique ID number, a weight for stably conveying the test tube, and others can be housed. Also, the test tube holder body housing and the bottom lid housing can have an outer diameter larger than that of the test tube to be conveyed and smaller than the width of the conveyor line. Note that the shape of the test tube holder body housing and the bottom lid housing may be, for example, a polygonal shape. Even in that case, a maximum length in a cross-sectional direction can be smaller than the width of the conveyor line. Particular test tube holder that may be used is described in EP 2 902 790 A1, the contents thereof concerning vessel carriers is incorporated by reference in this application.

As the first transporting portion and the second transporting portion can extend in different directions, the laboratory diagnostic vessel carrier may be transported from a higher level to a lower level with a change of the transporting direction. Particularly, as the first transporting portion and the second transporting portion are configured to transport the laboratory diagnostic vessel carrier by gravity, the laboratory diagnostic vessel carrier may be transported similar to a transporting process on a chute such that any conveyer belts may not be necessary within the transporting device for transporting the laboratory diagnostic vessel carrier. Needless to say, in order to allow the first transporting portion and the second transporting portion to transport a laboratory diagnostic vessel carrier by gravity, the configuration thereof can require a suitable material relative to the material of vessel carrier and a suitable inclination with respect to gravity. Further, as the first direction and the second direction can comprise opposite direction components, the transporting device can cause a reversal of the transporting direction for the vessel carrier. This can allow a more compact formation of the transporting device as the first transporting portion and the second transporting portion may be arranged not one behind the other such as in a row but one above the other.

The first transporting portion may comprise a first end, which can be configured to be connected to the first line portion, and a second end. The second transporting direction may comprise a third end and a fourth end, which can be configured to be connected to the second line portion. The transporting device may further comprise a stopping wall. The second end can face and can be spaced apart from the stopping wall. The third end can be arranged adjacent the stopping wall. Thus, a vessel carrier may be transported from the first end on the first transporting portion towards the stopping wall and from the stopping wall to the fourth end during operation. Thus, the reversal of the transporting direction for the vessel carrier can take place at the stopping wall.

The second end may be spaced apart from the stopping wall with a distance larger than a width of the laboratory diagnostic vessel carrier. Thus, the laboratory diagnostic vessel carrier can be allowed to enter the second transporting portion by falling through a gap between the second end of the first transporting portion and the stopping wall.

The stopping wall may comprise a stopper facing the first transporting portion. In other words, the stopper can protrude from the stopping wall towards the first transporting portion. Thus, a tilting of the laboratory diagnostic vessel carrier in the first direction when leaving the first transporting portion can be prevented.

The stopper may be at least partially made of an elastic material. Thus, an abrupt stopping of the laboratory diagnostic vessel carrier can be prevented and the laboratory diagnostic vessel carrier can be cushioned when engaging the stopper.

The stopper may comprise a tip made of the elastic material. Thus, the laboratory diagnostic vessel carrier may be cushioned at the tip when engaging the stopper as the tip can be that part of the stopper protruding furthermost towards the first transporting portion.

The third end may be connected to the stopping wall. Thus, the laboratory diagnostic vessel carrier can be directly forwarded from the stopping wall to the second transporting portion and aligned with the second direction by the stopping wall and its corresponding shape.

The transporting device may comprise two opposing side walls. The first transporting portion may comprise a sliding surface connected to the side walls and two sliding rails. The sliding rails may be respectively connected to one of the sidewalls such that an opening can be formed between the sliding rails. The sliding rails may be arranged adjacent the second end. Thus, the laboratory diagnostic vessel carrier may be forwarded from the stopping wall to the second transporting wall while an upper end of the laboratory diagnostic vessel carrier can pass through the opening. Accordingly, the upper end of the laboratory diagnostic vessel carrier may not hit the first transporting portion when moving on the second transporting portion. Thereby, the transporting device may be manufactured in a more compact manner, i.e. with a smaller height.

The sliding surface and the sliding rails may be connected to one another. Thus, a direct and smooth transition from the sliding surface to the sliding rails can be ensured without the risk of any obstructions.

In some embodiments, the sliding surface and the sliding rails may be integrally formed. Thus, an improved direct and smooth transition from the sliding surface to the sliding rails can be provided.

The second end may be located within a plane which can run substantially perpendicular to a direction connecting the first end and the fourth end and which can include a middle point of a distance between the first end and the fourth end. Thus, the laboratory diagnostic vessel carrier may be transported one half distance of the first line portion to the second line portion on the first transporting portion and the laboratory diagnostic vessel carrier may be transported the other half distance of the first line portion to the second line portion on the second transporting portion. Thus, the transporting portions may be symmetrically formed with respect to the specified plane.

The first transporting portion and the second transporting portion may be inclined relative to one another at an angle, in one embodiment, of about 30° to about 122° and, in another embodiment, of about 45° to about 90°. Thus, an improved transport by gravity can be provided.

The first transporting portion and/or the second transporting portion may be formed curved or straight. The form of the transporting portions can refer to the transporting surface thereof. While a straight formation may be easier to be manufactured, a curved formation can smooth the transition from the first transporting portion to the second transporting portion and from the second transporting portion to the second line portion.

The transporting device may be made of plastics or metal. Thus, the transporting device may be made of well-established materials having good sliding characteristics relative the common materials of the laboratory diagnostic vessel carrier.

The stopping wall may be configured to push the laboratory diagnostic vessel carrier such that the laboratory diagnostic vessel carrier can be aligned with the second direction. In other words, the stopping wall may be shaped so as to provide the laboratory diagnostic vessel carrier with an impulse by which the laboratory diagnostic vessel carrier can be oriented substantially parallel to the second direction. This kind orientation may be defined by a bottom surface of the laboratory diagnostic vessel carrier with which the laboratory diagnostic vessel carrier slides on the line portions of the transporting device. The impulse may cause a tilting of the laboratory diagnostic vessel carrier which can result in the alignment with the second direction. For example, the stopper of the stopping wall may extend in or substantially parallel to a direction of a bisecting line of an angle between the first transporting direction and the second transporting direction.

According to the disclosed conveying line, the conveying line can comprise at least a first line portion, a second line portion and a transporting device as specified above. The first line portion can be arranged above the second line portion with respect to a direction of gravity. The first transporting portion can be connected to the first line portion and the second transporting portion can be connected to the second line portion. Thus, a laboratory diagnostic vessel carrier may transported from the first line portion, which can be arranged on a higher level if compared to the second line portion, to the second line portion, which can be arranged on a lower level if compared to the first line portion, by gravity. Thus, any wearing constructional members for this transport can be avoided.

A transporting device for transporting a laboratory diagnostic vessel carrier from a first line portion to a second line portion of a conveying line is presented. The first line portion can be arranged above the second line portion with respect to a direction of gravity. The transporting device can comprise a first transporting portion and a second transporting portion. The first transporting portion can be configured to be connected to the first line portion and the second transporting portion can be configured to be connected to the second line portion. The first transporting portion can extend in a first direction and the second transporting portion can extend in a second direction different from the first direction. The first transporting portion and the second transporting portion can be configured to transport the laboratory diagnostic vessel carrier by gravity. The first direction can comprise at least a first component and the second direction can comprise at least a second component. The second component can be opposite to the first component.

The first transporting portion can comprise a first end, which can be configured to be connected to the first line portion, and a second end, wherein the second transporting direction can comprise a third end and a fourth end, which can be configured to be connected to the second line portion. The transporting device can further comprise a stopping wall. The second end can face and can be spaced apart from the stopping wall. The third end can be arranged adjacent the stopping wall.

The second end can be spaced apart from the stopping wall with a distance larger than a width of the laboratory diagnostic vessel carrier.

The stopping wall can comprise a stopper facing the first transporting portion. The stopper can be at least partially made of an elastic material. The stopper can comprise a tip made of the elastic material. The third end can be connected to the stopping wall.

The transporting device can further comprise two opposing side walls. The first transporting portion can comprise a sliding surface connected to the side walls and two sliding rails. The sliding rails can be respectively connected to one of the sidewalls such that an opening can be formed between the sliding rails. The sliding rails can be arranged adjacent the second end. The sliding surface and the sliding rails can be connected to one another. The sliding surface and the sliding rails can be integrally formed.

The second end can be located within a plane which can run substantially perpendicular to a direction connecting the first end and the fourth end and which can include a middle point of a distance between the first end and the fourth end.

The first transporting portion and the second transporting portion can be inclined relative to one another at an angle of, according to one embodiment, about 30° to about 122° and, in another embodiment, of about 45° to about 90°.

The first transporting portion and/or the second transporting portion can be formed curved or straight. The transporting device can be made of plastics or metal.

The stopping wall can be configured to push the laboratory diagnostic vessel carrier such that the laboratory diagnostic vessel carrier can be aligned with the second direction.

A transporting system can comprise a transporting device according to the embodiments above and a laboratory diagnostic vessel carrier. The laboratory diagnostic vessel carrier can be configured to be pushed by the stopping wall so to be aligned with the second direction.

A conveying line can comprise at least a first line portion, a second line portion and a transporting device according to the embodiments above. The first line portion can be arranged above the second line portion with respect to a direction of gravity. The first transporting portion can be connected to the first line portion and the second transporting portion can be connected to the second line portion.

Figure 1:
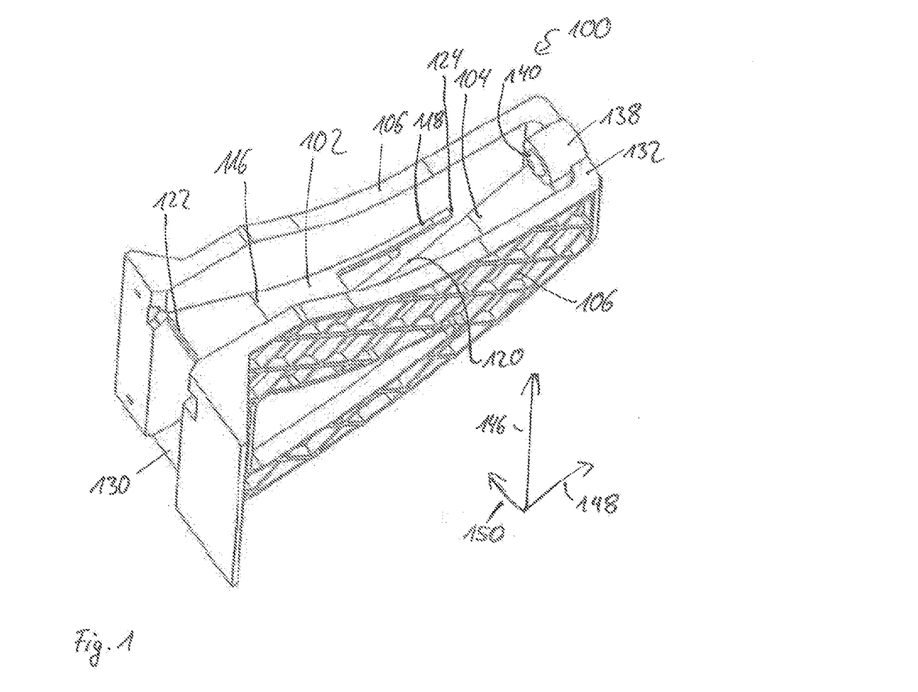
FIG. 1 illustrates a perspective view of a transporting device according to an embodiment of the present disclosure.
Figure 4:
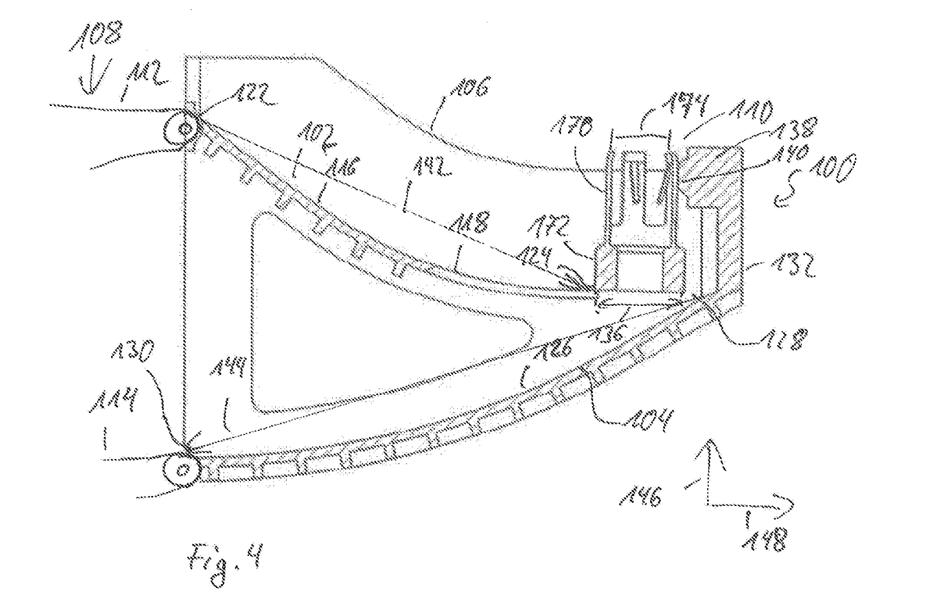
FIG. 4 illustrates a cross-sectional view of the transporting device taken along line A-A of FIG. 2 during operation according to an embodiment of the present disclosure.

Referring initially to FIG. 1, FIG. 1 shows a perspective view of a transporting device 100. The transporting device 100 can comprise a first transporting portion 102 and a second transporting portion 104. The transporting device 100 can further comprise two opposing sidewalls 106. As will be explained in further detail below, the transporting device 100 can be configured to be used with a conveying line 108 for transporting a laboratory diagnostic vessel carrier 110 (FIG. 4). The first transporting portion 102 can be configured to be connected to a first line portion 112 of the conveying line 108 and the second transporting portion 104 can be configured to be connected to a second line portion 114 of the conveying line 108 (FIG. 4).

Figure 2:
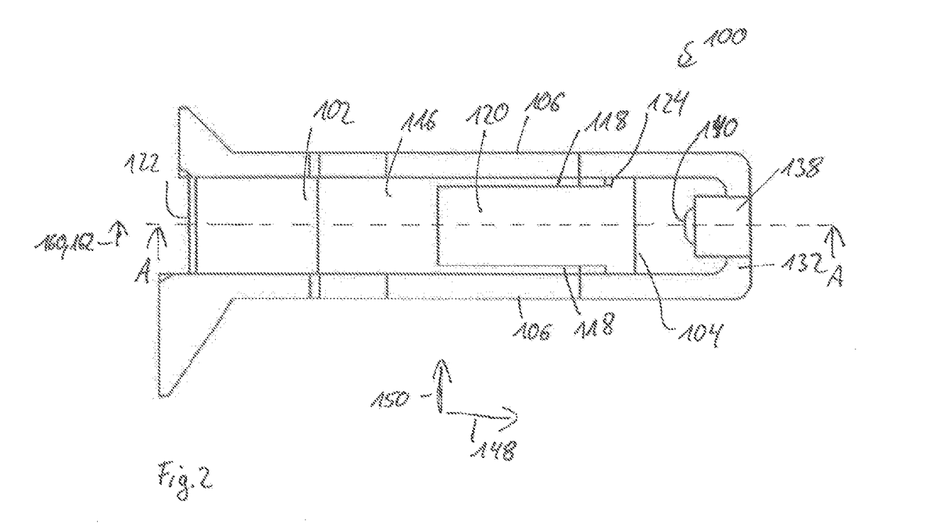
FIG. 2 illustrates a plan view of the transporting view according to an embodiment of the present disclosure.

FIG. 2 shows a plan view of the transporting device 100. The first transporting portion 102 and the second transporting portion 104 can respectively be arranged between the sidewalls 106. The first transporting portion 102 can comprise a sliding surface 116 and two sliding rails 118. The sliding surface 116 can be connected to the sidewalls 106. The sliding rails 118 can respectively be connected to one of the sidewalls 106. In other words, one of the sliding rails 118 can be connected to one of the sidewalls 106 while the other one of the sliding rails 118 can be connected to the other one of the sidewalls 106. Thereby, an opening 120 can be formed between the sliding rails 118. Further, the sliding surface 116 and the sliding rails 118 can be connected to one another. In one embodiment, the sliding surface 116 and the sliding rails 118 can be integrally formed. The sliding surface 116 and the sliding rails 118 may also be integrally formed with the sidewalls 106. The first transporting portion 104 can further comprise a first end 122, which can be configured to be connected to the first line portion 112, and a second end 124. The sliding surface 116 can extend from the first end 122 towards the second end 124. The sliding rails 118 can be arranged adjacent the second end 124.

Figure 3:
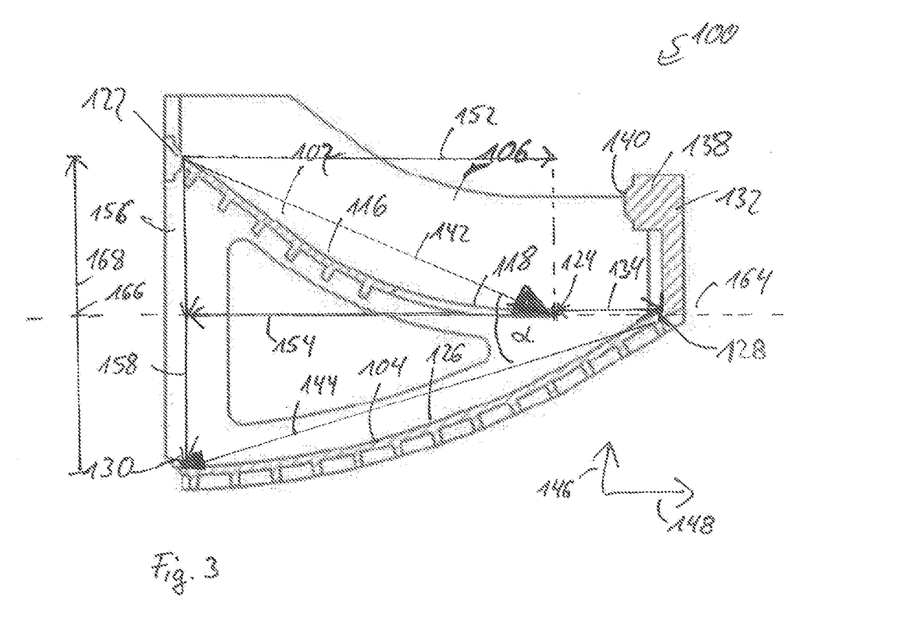
FIG. 3 illustrates a cross-sectional view of the transporting device taken along line A-A of FIG. 2 according to an embodiment of the present disclosure.

FIG. 3 shows a cross-sectional view of the transporting device 100 taken along line A-A of FIG. 2. The second transporting portion 104 can comprise a sliding surface 126. The sliding surface 126 can be connected to the sidewalls 106. The sliding surface 126 may also be integrally formed with the sidewalls 106. The second transporting portion 104 can comprise a third end 128 and a fourth end 130. The fourth end 130 can be configured to be connected to the second line portion 114.

The transporting device 100 can further comprise a stopping wall 132. The second end 124 of the first transporting portion 102 can face the stopping wall 132. The second end 124 of the first transporting portion 102 can be spaced apart from the stopping wall 132. In one embodiment, the second end 124 of the first transporting portion 102 can be spaced apart from the stopping wall 132 with a distance 134. The distance 134 can be larger than a width 136 of the laboratory diagnostic vessel carrier 110. The width 136 can correspond to a diameter of the laboratory diagnostic vessel carrier 110. The third end 128 of the second transporting portion 104 can be arranged adjacent the stopping wall 132. In one embodiment, the third end 128 of the second transporting portion 104 can be connected to the stopping wall 132. For example, the sliding surface 126 of the second transporting portion 104 and the stopping wall 132 can be integrally formed. The stopping wall 132 can comprise a stopper 138 facing the first transporting portion 102. The stopper 138 can at least be partially made of an elastic material. For example, the stopper 138 can comprise a tip 140 made of the elastic material. The elastic material may be rubber or a polymeric material.

As can be seen from FIG. 3, the first transporting portion 102 can extend in a first direction 142. The second transporting direction 104 can extend in a second direction 144. The second direction 144 can be different from the first direction as will be explained in further detail below. It can be noted that the first direction 142 and the second direction 144 may each be expressed by at least two components. In one embodiment, the transporting device 100 may be oriented in a manner such that the an imaginary line from the fourth end 130 to the first end 122 can define a positive direction of a z-axis 146, an imaginary line substantially perpendicular to the z-axis 146 and passing through the stopping wall 132 can define a x-axis 148, and an imaginary line substantially perpendicular to the z-axis 146 and the x-axis 148 can define a y-axis 150. It can be noted that in use of the transporting device 100, the z-axis can be substantially parallel to a direction of gravity. Gravity can act in a negative direction on the z-axis 146. Further, a positive direction of the x-axis 148 can be defined substantially perpendicular to a plane through the fourth end 130 and the first end 122 towards the stopping wall 132. Still further, a positive direction of the y-axis 150 can be defined substantially perpendicular to the sidewalls 106 and can correspond to a direction of view of FIG. 3.

The first direction 142 can comprise a first component 152 and the second direction 144 can comprise a second component 154. The second component 154 can be opposite to the first component 152. As shown in FIG. 3, the first transporting portion 102 can extend in the first direction 142. The first component 152 thereof can be in the positive direction of the x-axis 148. To the contrary, the second transporting portion 104 can extend in the second direction 146. The second component 154 thereof can be in the negative direction of the x-axis 148. Thus, with respect to the x-axis 148, the first component 152 of the first direction 144 can be opposite to the second component 154 of the second direction 144. The first direction 143 can also be defined by a third component 156, which can be in the negative direction of the z-axis 146. Similarly, the second direction 144 can also be defined by a fourth component 158, which can also be in the negative direction of the z-axis 146. It can be noted that a fifth component 160 of the first 142 direction and a sixth component 162 of the second direction 144 may be defined neither to be in the positive direction nor the negative direction of the y-axis 150 but may be defined so as to be zero in the direction of the y-axis 150.

The first transporting portion 102 and the second transporting portion 104 can be inclined relative to one another, in on embodiment, at an angle α of about 30° to about 120° and, in another embodiment, of about 45° to about 90° such as, for example, about 60°. As shown in FIG. 3, the first transporting portion 102 and the second transporting portion 104 can be formed curved. The curvature can be formed in the negative direction of the z-axis 146. In this case, the first direction 142 can be defined by an imaginary straight line from the first end 122 to the second end 124, whereas the second direction 144 can be defined by an imaginary straight line from the third end 126 to the fourth end 128. Alternatively, the first transporting portion 102 and the second transporting portion 104 can be formed straight. With the formation of the transporting device 100 shown in FIG. 3, the second end 124 can be located within a plane 164 which can run substantially perpendicular to a direction connecting the first end 122 and the fourth end 128, i.e. a direction of the z-axis 146, and which can include a middle point 166 of a distance 168 between the first end 122 and the fourth end 128. Basically, the transporting device 100 may be made of plastic, such as by injection molding, or may be made of metal. Basically, the transporting device 100 can be configured to transport the laboratory diagnostic vessel carrier 100 by gravity due to the inclined first transporting portion 102 and the second transporting portion 104 as will be explained in further detail below.

Figure 5:
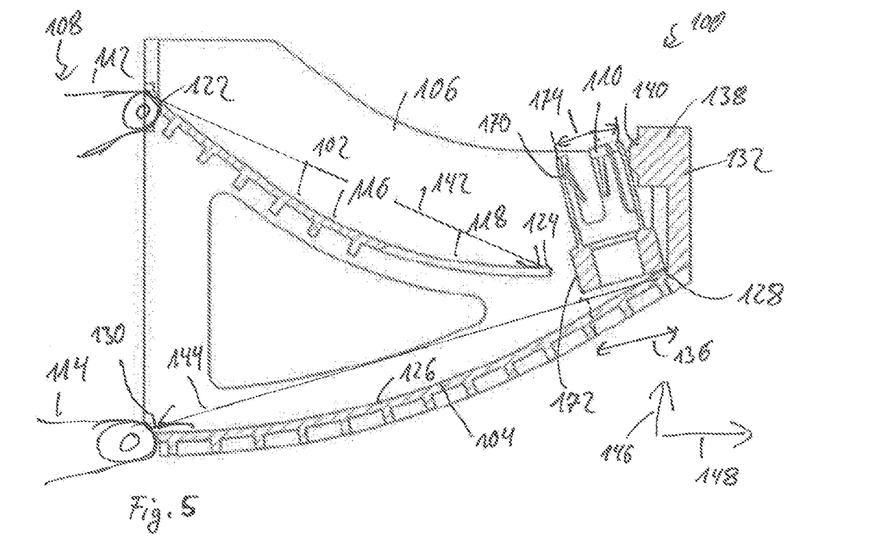
FIG. 5 illustrates a cross-sectional view of the transporting device taken along line A-A of FIG. 2 during operation according to an embodiment of the present disclosure.
Figure 6:
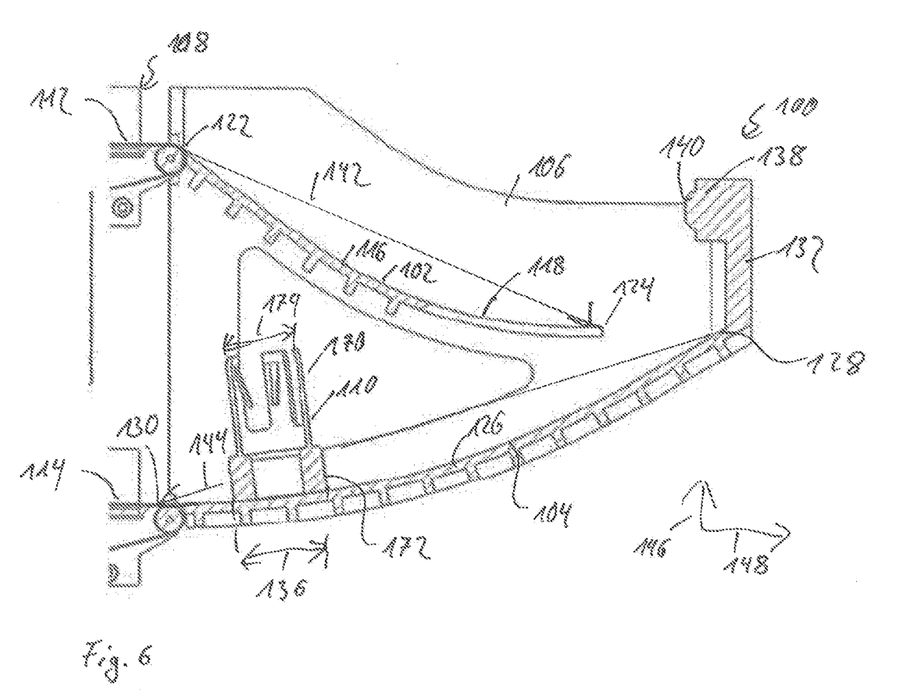
FIG. 6 illustrates a cross-sectional view of the transporting device taken along line A-A of FIG. 2 during operation according to an embodiment of the present disclosure.

FIGS. 4 to 6 show cross-sectional views of the conveying line 108 and the transporting device 100 taken along line A-A of FIG. 2 during different steps of operation. FIG. 4 shows a cross-sectional view of the conveying line 108 and the transporting device 100 taken along line A-A of FIG. 2 at the beginning of a transporting or conveying process on the transporting device 100. As can be seen from FIG. 4, the first line portion 112 can be arranged above the second line portion 114 with respect to a direction of gravity. The transporting device 100 can be configured to transport a laboratory diagnostic vessel carrier 110 from the first line portion 112 to the second line portion 114 as will be explained in further detail hereinafter. Prior to the state shown in FIG. 4, the transporting device 100 was connected to the conveying line 100 such that the first transporting portion 102 can be connected to the first line portion 112 of the conveying line 108 and the second transporting portion 104 can be connected to the second line portion 114 of the conveying line 108. The laboratory diagnostic vessel carrier 110 was conveyed on the first line portion 112 to the first end 122 of the first transporting portion 102, which can correspond to a transporting direction from the left to the right with respect to the illustration of FIG. 4. When entering the first transporting portion 102 at the first end 122, the laboratory diagnostic vessel carrier 110 can be transported on the sliding surface 116 and the sliding rails 118 in the first direction 142 by gravity. The laboratory diagnostic vessel carrier 110 can then engage the stopper 138 with an upper portion 170 thereof as shown in FIG. 4. The upper portion 170 can correspond to a housing of the test tube holder exemplarily representing the laboratory diagnostic vessel carrier 110. Basically, the upper portion 170 can define two upper third of the laboratory diagnostic vessel carrier 110.

FIG. 5 shows a cross-sectional view of the conveying line 108 and the transporting device 100 taken along line A-A of FIG. 2 at a subsequent step of the transporting or conveying process on the transporting device 100. While engaging the stopper 138 with the upper portion 170, the laboratory diagnostic vessel carrier 110 can be tilted counter-clockwise at a lower portion 172 thereof with respect to the illustration of FIG. 5. The lower portion 172 can correspond to a bottom lid housing of the test tube holder exemplarily representing the laboratory diagnostic vessel carrier 110. Basically, the lower portion 172 can define a lower third of the laboratory diagnostic vessel carrier 110. This tilting process can be caused as the upper portion 170 of the laboratory diagnostic vessel carrier 110 can be stopped by the stopper 138 at the stopping wall 132, whereas the lower portion 172 may still be moved in the first direction 142. Therefore the sliding surface of the lower portion 172 can be pre-aligned by the tilting process with the sliding surface 126 of the second transport portion 104. As the second end 124 is spaced apart from the stopping wall with the distance 134 larger than the width 136 of the laboratory diagnostic vessel carrier 110, a gap can be formed between the second end 124 of the first transporting portion 102 and the stopping wall 130. Thereby, the laboratory diagnostic vessel carrier 110 can fall downwards through this gap, which can correspond to a direction in the negative direction of the z-axis 146, and the laboratory diagnostic vessel carrier 110 can enter the second transporting portion 104 at the third end 128 as shown in FIG. 5.

FIG. 6 shows a cross-sectional view of the conveying line 108 and the transporting device 100 taken along line A-A of FIG. 2 at the end of the transporting or conveying process on the transporting device 100. When entering the second transporting portion 104 at the third end 128, the laboratory diagnostic vessel carrier 110 can be further tilted counter-clockwise at the lower portion 170 thereof with respect to the illustration of FIG. 6. Thereby, the laboratory diagnostic vessel carrier 110 can engage the sliding surface 126 of the second transporting portion 104 with its complete width 136. Due to this tilting process, the upper portion 170 of the laboratory diagnostic vessel carrier 110 can pass through the opening 120 between the sliding rails 118 of the first transporting portion 102 as the upper portion 104 comprises a smaller width 174 than the lower portion 172. Thus, the first transporting portion 102 may not obstruct a transporting process of the laboratory diagnostic vessel carrier 110 on the second transporting portion 104. Then, the laboratory diagnostic vessel carrier 110 can be transported on the sliding surface 126 in the second direction 144 by gravity. In one embodiment, the laboratory diagnostic vessel carrier 110 can be moved from the third end 128 to the fourth end 130. At the fourth end 130, the laboratory diagnostic vessel carrier 110 can enter the second line portion 114 and may be conveyed on the second line portion 114 in a transporting direction from the right to the left with respect to the illustration of FIG. 6. The transporting device 100 can allow transporting the laboratory diagnostic vessel carrier 110 from the first line portion 112, which can be arranged at a higher level if compared to the second line portion 114, to the second line portion exclusively by gravity. During this transport, a rotation of the laboratory diagnostic vessel carrier 110 around a longitudinal axis thereof can be prevented such that the laboratory diagnostic vessel carrier 110 can arrive with an identical orientation at the second line portion 114 as it has left the first line portion 112.

In further embodiments not shown, the first line portion 112 and the second line portion 114 may not be aligned as shown in the figures. For instance, they can be shifted laterally in both directions. Nevertheless these portions can be linked by an appropriate design of the transporting device.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A transporting device for transporting a laboratory diagnostic vessel carrier from a first line portion to a second line portion of a conveying line, wherein the first line portion is arranged above the second line portion with respect to a direction of gravity, the transporting device comprising:
   a first transporting portion; and
   a second transporting portion, wherein the first transporting portion is configured to be connected to the first line portion and the second transporting portion is configured to be connected to the second line portion, wherein the first transporting portion extends in a first direction and the second transporting portion extends in a second direction different from the first direction, wherein the first transporting portion and the second transporting portion are configured to transport the laboratory diagnostic vessel carrier exclusively by gravity, wherein first direction comprises at least a first component and the second direction comprises at least a second component, and wherein the second component is opposite to the first component.

2. The transporting device according to claim 1, wherein the first transporting portion comprises a first end configured to be connected to the first line portion and a second end, wherein the second transporting portion comprises a third end and a fourth end configured to be connected to the second line portion.

3. The transporting device according to claim 2, further comprising,
   a stopping wall, wherein the second end faces and is spaced apart from the stopping wall and wherein the third end is arranged adjacent the stopping wall.

4. The transporting device according to claim 3, wherein the second end is spaced apart from the stopping wall with a distance larger than a width of the laboratory diagnostic vessel carrier.

5. The transporting device according to claim 3, wherein the stopping wall comprises a stopper facing the first transporting portion.

6. The transporting device according to claim 5, wherein the stopper is at least partially made of an elastic material.

7. The transporting device according to claim 6, wherein the stopper comprises a tip made of the elastic material.

8. The transporting device according to claim 3, wherein the third end is connected to the stopping wall.

9. The transporting device according to claim 3, wherein the stopping wall is configured to push the laboratory diagnostic vessel carrier such that the laboratory diagnostic vessel carrier is aligned with the second direction.

10. The transporting device according to claim 2, wherein the second end is located within a plane which runs perpendicular to a direction connecting the first end and the fourth end and which includes a middle point of a distance between the first end and the fourth end.

11. The transporting device according to claim 1, wherein the first transporting portion and the second transporting portion are inclined relative to one another at an angle (a) of 30° to 120°.

12. The transporting device according to claim 1, wherein the first transporting portion and the second transporting portion are inclined relative to one another at an angle ($\alpha$) of 45° to 90°.

13. The transporting device according to claim 1, wherein the first transporting portion and/or the second transporting portion is formed curved or straight.

14. A conveying line, the conveying line comprising:
at least a first line portion;
a second line portion; and
a transporting device according to claim 1, wherein the first line portion is arranged above the second line portion with respect to a direction of gravity and wherein the first transporting portion is connected to the first line portion and the second transporting portion is connected to the second line portion.

15. A transporting device for transporting a laboratory diagnostic vessel carrier from a first line portion to a second line portion of a conveying line, wherein the first line portion is arranged above the second line portion with respect to a direction of gravity, the transporting device comprising:
a first transporting portion, wherein the first transporting portion comprises a first end configured to be connected to the first line portion and a second end;
a second transporting portion, wherein the first transporting portion is configured to be connected to the first line portion and the second transporting portion is configured to be connected to the second line portion, wherein the second transporting portion comprises a third end and a fourth end configured to be connected to the second line portion, wherein the first transporting portion extends in a first direction and the second transporting portion extends in a second direction different from the first direction, wherein the first transporting portion and the second transporting portion are configured to transport the laboratory diagnostic vessel carrier by gravity, wherein first direction comprises at least a first component and the second direction comprises at least a second component, and wherein the second component is opposite to the first component;
two opposing side walls, wherein the first transporting portion comprises a sliding surface connected to the side walls; and
two sliding rails, wherein the sliding rails are respectively connected to one of the sidewalls such that an opening is formed between the sliding rails and wherein the sliding rails are arranged adjacent the second end.

16. The transporting device according to claim 15, wherein the sliding surface and the sliding rails are connected to one another.

17. The transporting device according to claim 15, wherein the sliding surface and the sliding rails are integrally formed.

* * * * *